United States Patent [19]
Potter et al.

[11] Patent Number: 5,688,939
[45] Date of Patent: *Nov. 18, 1997

[54] PLANT ADENYLOSUCCINATE SYNTHETASE AND DNA CODING THEREFOR

[75] Inventors: Sharon Lee Potter, Raleigh; Eric R. Ward, Durham, both of N.C.

[73] Assignee: Novartis Finance Corporation

[*] Notice: The term of this patent shall not extend beyond the expiration date of Pat. No. 5,519,125.

[21] Appl. No.: 565,655

[22] Filed: Nov. 29, 1995

Related U.S. Application Data

[63] Continuation-in-part of Ser. No. 361,611, Dec. 22, 1994, Pat. No. 5,519,125.

[51] Int. Cl.$^6$ .............................. C12N 15/29; C12N 5/04; C12N 5/06; C12N 15/82; C12N 1/19; C12N 1/21

[52] U.S. Cl. .................... 536/23.6; 536/23.2; 435/69.1; 435/70.1; 435/71.1; 435/172.3; 435/252.3; 435/254.2; 435/320.1; 435/348; 435/419

[58] Field of Search ............................. 536/23.2, 23.6; 435/69.1, 70.1, 71.1, 172.3, 240.2, 240.4, 252.3, 254.2, 320.1, 419, 348

[56] References Cited

PUBLICATIONS

Aimi, J., et al., "Cloning of a cDNA Encoding Adenylosuccinate Lyase by Functional Complementation in *Esherichia coli*", *J. Biol. Chem.*, 265(16):9011–9014 (1990).

Bass, M.B., et al., "Overproduction, Purification, and Characterization of Adenylosuccinate Synthetase from *Esherichia coli*", Arch. *Biochem. Biophys.* 256:335–342 (1987).

Baugher, B.W., et al., "Changes in Isozymes of Adenylosuccinate Synthetase", *Biochem Biophy Res. Commun.* 94: 123–129 (1980).

D'Ovidio, R., et al., "Rapid and efficient detection of genetic polymorphism in wheat through amplification by polymerase chain reaction", *Plant Mol. Biol.* 15: 169–171 (1990).

Delauney, A.J., et al., "A soybean gene encoding $\Delta^1$–pyrroline–5–carboxylate reductase was isolated by functional complementation is *Escherichia coli* and is found to be osmoregulated", *Mol. Genet.* 221:299–305 (1990).

Dorfman, B., "The Isolation of Adenylosuccinate Synthetase Mutants in Yeasst by Selection for Constitutive Behavior in Pigmented Strains", *Genetics* 61:377–389 (1969).

Elledge, S.J., et al., "λYES: A multifunctional cDNA expression vector for the isolation of genes by complementation of yeast and *Escherichia coli* mutations," *Proc. Natl. Acad. Sci. USA* 88: 1731–1735 (1991).

Ellerström, M., et al., "Cloning of a cDNA for rape chloroplast 3–isoproplmalate dehydrogenase by genetic complementation in yeast", *Plant Mol. Biol.* 18: 557–566 (1992).

Frisch, D.A., et al., "Direct genetic selection of a maize cDNA for dihydrodipicolinate synthase in an *Escherichia coli dap A$^-$auxotroph*", *Mol. Gen. Genet.* 228:287–293 (1991).

Guicherit, O.M., et al., "Amplification of an Adenylosuccinate Synthetase Gene in Alanosine–resistant Murine T–Lymphoma Cells", *J. of Biol. Chem.* 269(6): 4488–4496 (1994).

Guicherit, O.M., et al., "Molecular Cloning and Expression of a Mouse Muscle cDNA Encoding Adenylosuccinate Synthetase", *J. of Biol. Chem.* 266(33): 22582–22587 (1991).

Helentjaris, T., et al., "Restriction fragment polymorphisms as probes for plant diversity and their development as tools for applied plant breeding", *Plant Mol. Biol.* 5: 109–118 (1985).

Helentjaris, T., "A genetic linkage map for maize based on RFLPs", *Trends Genet.* 3(8): 217 (1987).

Kohorn, B.D. et al., "A Hydrophobic, Carboxy–Proximal Region of a Light–Harvesting Chlorophyll a/b Protein Is Necessary for Stable Integration into Thylakoid Membranes", *Plant Cell* 1: 159–166 (1989).

Lehninger, A.L., "The Biosynthesis of Nucleotides", *Biochemistry*, Worth Publishers, NY:p. 743 (1975).

Li, H., et al., "Information for Targeting to the Chloroplastic Inner Envelope Membrane is Contained in the Mature Region of the Maize BT1–encoded Protein", *J. Biol. Chem.* 267:18999–19004 (1992).

Li, H., et al., "Targeting of Proteins to the Outer Envelope Membrane Uses a Different Pathway than Transport into Chloroplasts", *Plant Cell* 3: 709–717 (1991).

Lowenstein, J.M., "The Purine Nucleotide Cycle Revised", *Int. J. Sports Med.* 11:S37–S46 (1990).

Mäntsälä, P., et al., "Cloning and Sequence of *Bacillus subtilis purA* and *guaA*, Involved in the Conversion of IMP to AMP and GMP", *J. of Bacter.*, 174(6): 1883–1890 (1992).

Minet, M., et al., "Complementation of *Saccharomyces cerevisae* auxotrophic mutants by *Arabidopsis thaliana* cDNAs", *Plant J.* 2: 417–422 (1992).

Niyogi, K.K., et al., "Suppressors of trp1 Fluorescence Identify a New Arabidopsis Gene, TRP4, Encoding the Anthranilate Synthase β Subunit", *Plant Cell* 5: 1011–1027 (1993).

Powell, S.M., et al., "Cloning and characterization of the cDNA encoding human adenylosuccinate synthetase", *FEBS* 303(1): 4–10 (1992).

(List continued on next page.)

*Primary Examiner*—David T. Fox
*Attorney, Agent, or Firm*—Larry W. Stults

[57] ABSTRACT

The present invention provides novel plant DNA sequences coding for native adenylosuccinate synthetase (ADSS). Methods for using the complete or partial ADSS coding sequence as a probe for diagnostic, mapping and other purposes are taught. Generation of transformed host cells capable of expressing ADSS is also taught. Methods of using the transformed host cells are taught, including methods for recombinant production of ADSS enzymes. A method for using the plant ADSS enzyme to screen for inhibitors of ADSS activity is also provided.

13 Claims, No Drawings

OTHER PUBLICATIONS

Schnorr, K.M., et al., "Molecular characterization of the *Arabidopsis thaliana* cDNAs encoding three purine biosynthetic enzymes", *The Plant Journal*, 6(1): 113–121 (1994).

Schubert, K.R., "Products of Biological Nitrogen Fixation in Higher Plants: Synthesis, Transport, and Metabolism", *Annu. Rev. Plant Physiol.* 37: 539–574 (1986).

Senecoff, J.F., et al., "Isolating the *Arabidopsis thaliana* Genes for de Novo Purine Synthesis by Suppression of *Escherichia coli* Mutants", *Plant Physiol.* 102:387–399 (1993).

Snustad, D.P., et al., "Maize Glutamine Synthetase cDNAs: Isolation by Direct Genetic Selection in *Escherichia coli*", *Genetics* 120:1111–1124 (1988).

Sommer, S.S., et al., "PCR Amplification of Specific Alleles (PASA) is a General Method for Rapidly Detecting Known Single–Base Changes", *BioTechniques* 12(1): 82–87 (1992).

Poland, B.W., et al., "Crystal Structure of Adenylosuccinate Synthetase from *Escherichia coli*", *J. Biol. Chem.*, 268(34): 25334–25342 (1993).

Stayton, M.M., et al., "Regulation, Genetics, and Properties of Adenylosuccinate Synthetase: A Review", *Curr. Top. Cell. Regul.* 22: 103–141 (1983).

Wiesmüller, L., et al., "Purification and cDNA–derived Sequence of Adenylosuccinate Synthetase from *Dictyostelium discoideum*", *J. of Biol. Chem.* 266(4): 2480–2485 (1991).

Wolfe, S.A., et al., "Nucleotide Sequence and Analysis of the purA Gene Encoding Adenylosuccinate Synthetase of *Escherichia coli* K12", *J. of Biol. Chem.* 263(35): 19147–19153 (1988).

Hatch, M.D., "Inhibition of Plant Adenylosuccinate Synthetase by Hadacidin and the Mode of Action of Hadacidin and Structurally Related Compounds on Plant Growth", *Phytochemistry*, 6:115–119 (1967).

Sasaki et al., "Toward cataloguing all rice genes: large–sace sequencing of randomly chosen rice cDNAs from a callus cDNA library", DDBJ Database entry, accession number D15352 (May 1993) Plant J 6: 615–624 (1994).

PLANT ADENYLOSUCCINATE SYNTHETASE AND DNA CODING THEREFOR

CROSS REFERENCE TO RELATED APPLICATIONS

This application is a continuation-in-part of application Ser. No. 08/361,611 filed Dec. 22, 1994, now U.S. Pat. No. 5,519,125.

FIELD OF THE INVENTION

The invention relates generally to an enzymatic activity involved in adenosine 5'-monophosphate biosynthesis in plants. In particular, the invention relates to the plant enzyme which catalyzes the synthesis of adenylosuccinate and the gene encoding this enzyme. In one aspect, the invention relates to the recombinant production of this enzyme in a heterologous host. In another aspect, the invention is applied to the identification of new herbicides. In yet another aspect, the invention relates to the development of genetic markers in plants.

BACKGROUND OF THE INVENTION

Adenosine 5'-monophosphate (AMP, also known as adenylic acid) is a precursor of adenosine 5'-triphosphate (ATP), the key energy carrying molecule for all living systems. The first committed enzymatic step in the biosynthesis of AMP is the synthesis of adenylosuccinate from inosine 5'-monophosphate (IMP; inosinic acid) and aspartate. The enzyme which catalyzes this step is known as adenylosuccinate synthetase (IMP:L-aspartate ligase(GDP-forming), EC 6.3.4.4, referred to herein as "ADSS").

In *E. coli*, ADSS is a dimer of identical 48 kD subunits. Its three-dimensional structure has been determined to 2.8 Å resolution (Poland et al., *J. Biol. Chem.* 268:25334–25342 (1993). In mammalian cells, the ADSS enzyme is present as two isoforms. An acidic form, present in non-muscle tissues, is thought to be involved in de novo production of AMP. A basic form, present in muscle tissue, thought to act as part of the purine nucleotide cycle, which involves interconversion of IMP and AMP with the net result of deaminating aspartate to fumarate (Lehninger, *Biochemistry*. Worth Publishers, NY (1975), p. 743; Lowenstein, *Int. J. Sports Med.* 11: S36–S46 (1990).

Genes encoding the ADSS enzyme have been isolated from a variety of species including *E. coli* (Wolfe and Smith, J. Biol. Chem. 263: 19147–19153 (1988)), *D. discoideum* (Weismuller et al., *J. Biol. Chem.* 266: 2480–2485 (1991)), mouse (Guicherit et al., *J. Biol. Chem.* 266: 22582–22587 (1991); Guicherit et al., *J. Biol. Chem.* 269: 4488–4496 (1994), *Bacillus subtilus* (Maentsaelae and Zalkin, *J. Bacteriol.* 174: 1881–1890 (1992), human (Powell et al., *FEBS Lett.* 303: 4–10 (1992), *S. cerevisiae* (Genbank accession no. L22185), and *Caenorhabditis elegans* (EST; Genbank accession no. M75738). However, genes encoding the ADSS enzyme have heretofore not been isolated from any plant species.

Presently, too little is known about the plant ADSS enzyme and its relationship to the ADSS enzymes/genes which have been isolated from other organisms to allow isolation of ADSS encoding genes from any plant species using known approaches.

Methods for isolating genes which are based upon knowledge of the structure of the proteins they encode cannot be applied to plant ADSS genes because too little is presently known about plant ADSS enzymes. Metabolic enzymes such as ADSS are typically very difficult to purify from plants because of their extremely low abundance. In addition, the presence of various phenolic and carbohydrate compounds in plants can interfere with the isolation of pure enzyme with native activity.

In the absence of direct structural information, a number of standard techniques are available for the isolation of proteins and their corresponding genes. Such standard techniques include nucleic acid hybridization and amplification by polymerase chain reaction using oligonucleotide primers corresponding to conserved amino acid sequence motifs. Unfortunately, these techniques would not be expected to be useful for isolation of plant ADSS genes because they rely upon the presence of significant structural similarity (i.e. amino acid and DNA sequence) with known proteins and genes that have the same function. Since there is no significant structural similarity even among the known ADSS genes and proteins from non-plant organisms (see, e.g. Powell et al., *FEBS Lett.* 303: 4–10 (1992)) it is unlikely that these proteins would share any significant structural similarity with plant ADSS proteins.

Another approach that has been used to isolate biosynthetic genes in other metabolic pathways from higher eukaryotes is the complementation of microbial mutants deficient in the activity of interest. For this approach, a library of cDNAs from the higher eukaryote is cloned in a vector that can direct expression of the cDNA in the microbial host. The vector is then transformed or otherwise introduced into the mutant microbe, and colonies are selected that are phenotypically no longer mutant.

This strategy has worked for isolating genes from higher eukaryotes that are involved in several metabolic pathways, including histidine biosynthesis (e.g. U.S. patent application Ser. No. 08/061,644 to Ward et al., incorporated by reference herein in its entirety), lysine biosynthesis (e.g. Frisch et al., *Mol. Gen. Genet.* 228: 287 (1991)), purine biosynthesis (e.g. Aimi et al., *J. Biol. Chem.* 265: 9011 (1990)), and tryptophan biosynthesis (e.g. Niyogi et al., *Plant Cell* 5: 1011 (1993)). This strategy has also been used to isolate plant genes including those coding for maize glutamine synthase (Snustad et al, *Genetics* 120:1111–1114 (1988)), soybean -pyrroline -5-carboxylate reductase (Delauney et al., *Mol. Genet.* 221:299–305 (1990), maize dihydrodipicolinate synthase (Frisch et al., *Mol. Gen. Genet.* 228:287–293(1991)), rape chloroplast 3-isopropylmalate dehydrogenase (Eller et al., *Plant Mol. Biol.* 18:557–566 (1992); *Proc. Natl. Acad. Sci, USA* 88:1731–1735 (1991)), and dihydroorotate dehydrogenase (Minet et al., *Plant J.* 2:417–422 (1992)).

Microbial mutants thought to be defective in ADSS activity are available (e.g. *E. coil* purA mutant designated CGCS 5408 and *E. coli* strains CGCS 4431 and 7039 from *E. coli* Genetic Stock Center, Yale Univ.; yeast ade12 mutants reported in Dorfman, *Genetics* 61:377–389 (1969)). However, despite the availability of these mutants, application of the complementation technique to isolate cDNAs encoding ADSS enzymatic activity has proven to be unsuccessful for avian (Powell et al., *FEBS Lett.* 303: 4–10 (1992)) and *B. subtilis* ADSS (Maentsaelae and Zalkin, *J. Bacteriol.* 174: 1881–1890 (1992).

There are several reasons which may explain the failure of this complementation strategy when applied to ADSS, particularly eukaryotic ADSS genes. First, the eukaryotic ADSS cDNA sequence may not be expressed at adequate levels in the mutant microbe, for instance because of codon usage inconsistent with the usage preferences of the microbial host. Second, the primary translation product from the cloned eukaryotic coding sequence may not produce a functional polypeptide, for instance if activity requires a post-translational modification, such as glycosylation, that is not carried out by the microbe. Third, the heterologous protein expressed in *E. coli* may also be lethal to the cells in which it is expressed, thus rendering its isolation impossible. Fourth, the eukaryotic protein may fail to assume its active conformation in the microbial host, for instance if the protein is normally targeted to a specific organellar membrane system that the microbial host specifically lacks. This last possibility is especially likely for the plant ADSS enzyme, which has been associated in the plant cell with organelles not present in microbial hosts used in the complementation assay (Schubert, *Annu. Rev. Plant Physiol.* 37:539–574 (1986), and presumably reaches that organellar system as a result of a post-translational targeting mechanism involving both an N-terminal transit sequence, and intrinsic properties of the mature polypeptide (see, e.g. Kohorn and Tobin, *Plant Cell* 1: 159 (1989); Li et al., *Plant Cell* 3: 709 (1991); Li et al., *J. Biol. Chem.* 267: 18999 (1992)). Moreover, two other purine biosynthetic genes isolated from plants, 5'-phosphoribosyl-5-aminoimdazole synthetase (Senecoff and Meagher, *Plant Physiol.* 102:387–399 (1993)) and glycinamide synthetase (Schnorr et al., *Plant J.* 6:113–121 (1994)) also appear encode proteins that are targeted to the chloroplast.

SUMMARY OF THE INVENTION

The present invention provides an isolated DNA molecule encoding the adenylosuccinate synthetase (ADSS) enzyme from a plant source.

The DNA coding sequences for ADSS enzymes in *Arabidopsis thaliana*, *Zea mays* and wheat are provided in SEQ ID NOS: 1, 3 and 5, respectively. Using the information provided by the present invention, the DNA coding sequence for the adenylosuccinate synthetase (ADSS) enzyme from any plant source may now be obtained using standard methods.

The present invention also encompasses the recombinant production of the ADSS enzyme, and methods for using recombinantly produced ADSS. In particular, the present invention provides methods of using purified ADSS to screen for novel herbicides which affect the activity of ADSS.

The present invention is further directed to probes and methods for detecting the presence and form of the ADSS gene and quantitating levels of ADSS transcripts in an organism. These methods may be used to diagnose disease conditions which are associated with an altered form of the ADSS enzyme or altered levels of expression of the ADSS enzyme.

DETAILED DESCRIPTION OF THE INVENTION

In one aspect, the present invention is directed to an isolated DNA molecule which encodes a eukaryotic form of adenylosuccinate synthetase (referred to herein as "ADSS"), the enzyme which catalyzes the synthesis of adenylosuccinate from IMP. The DNA coding sequence and corresponding amino acid sequence for an ADSS enzyme from *Arabidopsis thaliana* is provided as SEQ ID NOS: 1 and 2, respectively. The DNA coding sequence and corresponding amino acid sequence for a maize ADSS enzyme is provided as SEQ ID NOS:3 and 4, respectively. The DNA coding sequence and corresponding amino acid sequence for a wheat ADSS enzyme is provided as SEQ ID NOS:5 and 6, respectively.

The DNA encoding the ADSS enzyme may be isolated from the genome of any plant species desired according to the invention. One method taught for isolating a plant ADSS coding sequence is represented by Example 1. In this method cDNA clones encoding an ADSS enzyme are identified from a library of cDNA clones derived from the eukaryote of interest based on their ability to supply ADSS enzymatic activity to a mutant host organism deficient in this activity. Suitable host organisms for use in this method are those which can be used to screen cDNA expression libraries and for which mutants deficient in ADSS activity are either available or can be routinely generated. Such host organisms include, but are not limited to, *E. coli* and yeast.

Alternatively, plant ADSS coding sequences may be isolated according to well known techniques based on their sequence homology to the *Arabidopsis thaliana* (SEQ ID NO:1), *Zea mays* (SEQ ID NO:3), or wheat (SEQ ID NO:5) ADSS coding sequences taught by the present invention. In these techniques all or part of the known ADSS coding sequence is used as a probe which selectively hybridizes to other ADSS coding sequences present in population of cloned genomic DNA fragments or cDNA fragments (i.e. genomic or cDNA libraries) from a chosen organism. Such techniques include hybridization screening of plated DNA libraries (either plaques or colonies; see, e.g., Sambrook et al., "Molecular Cloning", eds., Cold Spring Harbor Laboratory Press, (1989)) and amplification by PCR using oligonucleotide primers corresponding to sequence domains conserved among known ADSS amino acid sequences (see, e.g. Innis et al., "PCR Protocols, a Guide to Methods and Applications", pub. by Academic Press (1990)). These methods are particularly well suited to the isolation of ADSS coding sequences from organisms closely related to the organism from which the probe sequence is derived. Thus, application of these methods using the Arabidopsis, *Zea mays* or wheat coding sequence as a probe would be expected to be particularly well suited for the isolation of ADSS coding sequences from other plant species.

The isolated plant ADSS sequences taught by the present invention may be manipulated according to standard genetic engineering techniques to suit any desired purpose. For example, the entire ADSS sequence or portions thereof may be used as probes capable of specifically hybridizing to ADSS coding sequences and messenger RNAs. To achieve specific hybridization under a variety of conditions, such probes include sequences that are unique among ADSS coding sequences and are at least 10 nucleotides in length, preferably at least 20 nucleotides in length, and most preferably at least 50 nucleotides in length. Such probes may be used to amplify and analyze ADSS coding sequences from a chosen organism via the well known process of polymerase chain reaction (PCR). This technique may be useful to isolate additional ADSS coding sequences from a desired organism or as a diagnostic assay to determine the presence of ADSS coding sequences in an organism. This technique may also be used to detect the presence of altered ADSS coding sequences in a plant associated with a particular condition of interest such as herbicide resistance, AMP deficiency, poor health, etc.

ADSS specific hybridization probes may also be used to map the location of the native ADSS gene(s) in the genome of a chosen plant using standard techniques based on the selective hybridization of the probe to genomic ADSS sequences. These techniques include, but are not limited to, identification of DNA polymorphisms identified or contained within the ADSS probe sequence, and use of such polymorphisms to follow segregation of the ADSS gene relative to other markers of known map position in a mapping population derived from self fertilization of a hybrid of two polymorphic parental lines (see e.g. Helentjaris et al., *Plant Mol. Biol.* 5: 109 (1985); Sommer et al. *Biotechniques* 12:82 (1992); D'Ovidio et al., *Plant Mol. Biol.* 15: 169 (1990)). While any plant ADSS sequence is contemplated to be useful as a probe for mapping ADSS genes, preferred probes are those ADSS sequences from plant species more closely related to the chosen plant species, and most preferred probes are those ADSS sequences from the chosen plant species. Mapping of ADSS genes in this manner is contemplated to be particularly useful for breeding purposes. For instance, by knowing the genetic map position of a mutant ADSS gene that confers herbicide resistance, flanking DNA markers can be identified from a reference genetic map (see, e.g., Helentjaris, *Trends Genet.* 3: 217 (1987)). During introgression of the herbicide resistance trait into a new breeding line, these markers can then be used to monitor the extent of ADSS-linked flanking chromosomal DNA still present in the recurrent parent after each round of back-crossing.

ADSS specific hybridization probes may also be used to quantitate levels of ADSS mRNA in a plant using standard techniques such as Northern blot analysis. This technique may be useful as a diagnostic assay to detect altered levels of ADSS expression that may be associated with particular conditions such as deficiencies in adenylosuccinate or AMP levels or enhanced tolerance to herbicides which target ADSS.

For recombinant production of the enzyme in a host organism, the plant ADSS coding sequence may be inserted into an expression cassette designed for the chosen host and introduced into the host where it is recombinantly produced. The choice of specific regulatory sequences such as promoter, signal sequence, 5' and 3' untranslated sequences, and enhancer appropriate for the chosen host is within the level of skill of the routineer in the art. The resultant molecule, containing the individual elements linked in proper reading frame, may be inserted into a vector capable of being transformed into the host cell. Suitable expression vectors and methods for recombinant production of proteins are well known for host organisms such as *E. coil* (see, e.g. Studier and Moffatt, *J. Mol. Biol.* 189: 113 (1986); Brosius, *DNA* 8: 759 (1989)), yeast (see, e.g., Schneider and Guarente, *Meth. Enzymol.* 194: 373 (1991)) and insect cells (see, e.g., Luckow and Summers, *Bio/Technol.* 6: 47 (1988)). Specific examples include plasmids such as pBluescript (Stratagene, La Jolla, Calif.), pFLAG (International Biotechnologies, Inc., New Haven, Conn.), pTrcHis (Invitrogen, La Jolla, Calif.), and baculovirus expression vectors, e.g., those derived from the genome of *Autographica californica* nuclear polyhedrosis virus (AcMNPV). A preferred baculovirus/insect system is pV111392/Sf21 cells (Invitrogen, La Jolla, Calif.).

Recombinantly produced plant ADSS enzyme can be isolated and purified using a variety of standard techniques. The actual techniques which may be used will vary depending upon the host organism used, whether the ADSS enzyme is designed for secretion, and other such factors familiar to the skilled artisan (see, e.g. chapter 16 of Ausubel, F. et al., "Current Protocols in Molecular Biology", pub. by John Wiley & Sons, Inc. (1994).

Recombinantly produced plant ADSS enzyme is useful for a variety of purposes. For example, it may be used to supply ADSS enzymatic activity in vitro to synthesize adenylosuccinate. In vitro synthesis of adenylosuccinate may be accomplished by reacting IMP, GTP, and aspartate in the presence of ADSS enzyme in an appropriate buffer, containing a divalent cation such as $Mg^{2+}$ (see, e.g. Baugher et al. *Biochem. Biophys. Res. Commun.* 94: 123–129 (1980); Stayton et al. *Curr. Top. Cell. Regul.* 22:103–141 (1983); Bass et al., *Arch. Biochem. Biophys.* 256:335–342 (1987)). The adenylosuccinate produced is a useful reagent which may be used as a substitute for purified adenylosuccinic acid previously available commercially from other sources.

Recombinantly produced plant ADSS enzyme may also be used in an in vitro assay to screen known herbicidal chemicals whose target has not been identified to determine if they inhibit ADSS. Such an in vitro assay may also be used as a more general screen to identify chemicals which inhibit ADSS activity and which are therefore herbicide candidates. Alternatively, recombinantly produced ADSS may be used to elucidate the complex structure of this enzyme. Such information regarding the structure of the ADSS enzyme may be used, for example, in the rational design of new inhibitory herbicides.

Typically, the inhibitory effect on ADSS is determined by a reduction or complete inhibition of adenylosuccinate synthesis in the in vitro assay (see, e.g. Baugher et al. *Biochem. Biophys. Res. Commun.* 94:123–129 (1980); Stayton et al. *Curr. Top. Cell. Regul.* 22:103–141 (1983); Bass et al., *Arch. Biochem. Biophys.* 256:335–342 (1987)). Such a determination may be made simply by comparing the amount of adenylosuccinate synthesized in the in vitro assay in the presence and absence of the candidate inhibitor.

The invention will be further described by reference to the following detailed examples. These examples are provided for purposes of illustration only, and are not intended to be limiting unless otherwise specified.

EXAMPLES

Standard recombinant DNA and molecular cloning techniques used here are well known in the art and are described by T. Maniatis, E. F. Fritsch and J. Sambrook, *Molecular Cloning: A Laboratory manual*, Cold Spring Harbor laboratory, Cold Spring Harbor, NY (1982) and by T. J. Silhavy, M. L. Berman, and L. W. Enquist, *Experiments with Gene Fusions*, Cold Spring Harbor Laboratory, Cold Spring Harbor, NY (1984) and by Ausubel, F. M. et al., *Current Protocols in Molecular Biology*, pub. by Greene Publishing Assoc. and Wiley-Interscience (1987).

Example 1

Isolation of Arabidopsis cDNAs encoding ADSS genes by functional complementation of an *E. coli* mutant.

An *Arabidopsis thaliana* (Landsberg) cDNA library in the plasmid vector pFL61 (Minet et al., *Plant J.* 2:417–422 (1992)) was obtained and amplified. The *E. coil* purA mutant PC0543 (CGSC #5408; *E. coli* Genetics Stock Center, Yale University, New Haven, Conn.) was obtained and maintained on N agar. The plasmid libraries were transformed into CGSC #5408 by electroporation using the Bio-Rad Gene Pulser and the manufacturer's conditions. The cells were plated on minimal E agar (Vogel and Bonner, *J. Biol. Chem.* 218:97–106 (1956) containing 100 mg/ml ampicillin and 0.4% casamino acids at a density of approximately 10,000,000 transformants/10 cm plate. Adenine prototrophs were recovered at a frequency of $1/6 \times 10^7$ from the pFL61 library. Plasmid DNA was isolated from the colony for sequence analysis. Purified plasmid DNA was shown to transform CGSC #5408 to purine prototrophy at high frequency. The purified plasmid complemented two additional *E. coli* purA mutants: ES4 (CGSC #4431; *E. coli* Genetics Stock Center, Yale University, New Haven, Conn.) and TX595 (CGSC #7039; *E. coli* Genetics Stock Center, Yale University, New Haven, Conn.), further confirming that it encoded a functional ADSS enzyme.

A restriction digest revealed that the cDNA insert was greater than 3 kB; sequence analysis revealed that the cDNA was chimeric, containing at the 3' end 1512 bp preceded by a polyA region. This 1512 bp region encodes an incomplete ADSS containing the mature protein sequence and a partial probable chloroplast transit peptide. A database search with the GAP program (Deveraux et al., *Nucleic Acids Res.* 12:387–395 (1984) reveals homology with the ADSS from *S. cerevisiae*. The two proteins are 70% similar, 51% identical with regions of high homology. The protein is 65% similar, 44% identical with *E. coli* ADSS.

ADSS-1, in the pBluescript SK vector, was deposited Sep. 22, 1994 as pWDC-6 (NRRL #B-21328).

The complete Arabidopsis cDNA sequence encoding ADSS-1 is set forth in SEQ ID NO:1. With the exception of the first four nucleotides, this sequence is contained in pWDC-6. The ADSS-1 amino acid sequence encoded by this cDNA is set forth in SEQ/D NO: 2.

Example 2

Isolation of Maize cDNAs encoding ADSS genes based on sequence homology to Arabidopsis ADSS.

A custom-made Unizap *Zea Mays* (cv. Blizzard) cDNA library was purchased from Clontech. Approximately 160,000 pfu of the phage library was plated at a density of 8,000 plaques per 10 cm Petri dish, and duplicate filter lifts were made onto nitrocellulose membrane (Scheiller and Scheull) after approximately 7 hours growth at 37° C. The filter lifts were probed with a PCR amplified fragment of the Arabidopsis ADSS cDNA labeled with $^{32}$P-dCTP by the random priming method (Life Technologies, Bethesda, Md.). Hybridization and wash conditions were at 50° C. as described in Church and Gilbert, *Proc. Natl. Acad. Sci. USA* 81: 1991–1995 (1984). After purification to single positively hybridizing plaques, plasmids were in vivo excised and cDNA inserts sequenced using dideoxy terminators labeled with fluorescent dyes (Applied Biosystems, Inc., Foster City, Calif.). The sequence thus obtained for the maize ADSS cDNA and the protein it encodes are provided as SEQ ID NOS:3 and 4, respectively. A plasmid containing this maize ADSS cDNA insert was deposited Oct. 24, 1994 as pWDC-9 (NRRL #B-21349).

Example 3

Isolation of Wheat cDNAs encoding ADSS genes based on sequence homology to Maize ADSS A custom made Unizap Triticum aestivum (cv Kanzler) cDNA library was purchased from Clontech. Approximately 50,000 pfu of the phage library was plated at a density of 5,000 plaques per 10 cm Petri dish, and duplicate filter lifts were made onto nitrocellulose membrane (Scheiller and Scheull) after approximately 7 hours growth at 37° C. The filter lifts were probed with a 1005 base pair EcoRI, XbaI restriction fragment from the 5' end of the maize ADSS cDNA labeled with 32P-dCTP by the random priming method (Life Technologies, Bethesda, Md.). Hybridization and wash conditions were at 50° C. as described in Church and Gilbert (1984), supra. After purification to single positively hybridizing plaques, plasmids were in vivo excised and cDNA inserts sequenced using dideoxy terminators labeled with fluorescent dyes (Applied Biosystems, Inc., Foster City, Calif.). The sequence thus obtained for the wheat ADSS cDNA and the protein it encodes are provided as SEQ ID NOS: 5 and 6, respectively. This wheat ADSS cDNA is not full-length but it includes the entire coding sequence for the mature ADSS protein which begins at approximately amino acid 35 of SEQ ID NO: 6 based on information obtained by N-terminal sequencing of the mature protein purified from wheat germ. Based on its homology to maize ADSS, the wheat ADSS cDNA lacks coding sequence for nine amino acids of a contemplated chloroplast transit peptide which is not present in the mature protein. A plasmid containing this wheat ADSS cDNA insert was deposited Nov. 3, 1995 as pWDC-10 (NRRL #B-21505).

Example 4

Isolation of additional ADSS genes based on sequence homology to known ADSS coding sequences A phage or plasmid library is plated at a density of approximately 10,000 plaques on a 10 cm Petri dish, and filter lifts of the plaques are made after overnight growth of the plates at 37° C. The plaque lifts are probed with one of the cDNAs set forth in SEQ ID NOS:1, 3, 5, or a portion of such a cDNA exhibiting high sequence conservation among the elucidated plant ADSS sequences. The cDNA probe is labeled with $^{32}$P-dCTP by the random priming method by means of a PrimeTime kit (International Biotechnologies, Inc., New Haven, Conn.). Hybridization conditions are 7% sodium dodecyl sulfate (SDS), 0.5M NaPO4 pH 7.0, 1 mM EDTA at 50° C. After hybridization overnight, the filters are washed with 2×SSC, 1% SDS. Positively hybridizing plaques are detected by autoradiography. After purification to single plaques, cDNA inserts are isolated, and their sequences determined by the chain termination method using dideoxy terminators labeled with fluorescent dyes (Applied Biosystems, Inc., Foster City, Calif.).

The standard experimental protocol described above can be used by one of skill in the art to obtain ADSS genes sequentially homologous to the known ADSS coding sequences from any other eukaryote, particularly other higher plant species.

An alignment of the amino acid sequences of the Arabidopsis, maize and wheat proteins (SEQ ID NOS: 2,4 and 6, respectively) is set forth in Table 1. An alignment of the nucleotide sequences encoding these proteins (SEQ ID NOS: 1,3 and 5, respectively) is set forth in Table 2. For each alignment the Arabidopsis sequence is used as the reference sequence. Gaps inserted into the sequences to obtain optimal alignment are indicated by dashes. Sequences identical to the Arabidopsis sequence in the maize and wheat sequences are denoted by a period and nonidentical sequences are shown.

TABLE 1

Comparison of the Arabidopsis (SEQ ID NO:2), Maize (SEQ ID NO:4) and Wheat (SEQ ID NO:6) S-1 Amino Acid Sequences
Identical residues are denoted by a period. Gaps in the alignment are indicated by a dash.

```
                      10            20            30            40            50
                       *             *             *             *             *
Arabidopsis  M S L S S L T L D S N P R F A V G G P Y H R R Y P P L H H P R S F V S C S - - - A K P P A V S A S L S V A A D S A A T E
Maize        . . . . T . - - - . H . A A . . A A . S G K S L F . A G P A A Q . V H F P K - - - . R L . V P A . - - - . S . A T . . V H
Wheat        - - - - - - - - - - - - A . A A A G R G . S F S . A A P A P . S . R L P G R Q . P A . . A A S A . A . E . . P . . - -

60            70            80            90           100           110
                       *             *             *             *             *             *
             S L G R I G S L S Q V S G V L G C Q W G D E G K G K L V D I L A Q H F D I V A R C Q G G A N A G H T I Y N S E G K K F A
             A E D . V S . . T . . . . . . . S . . . . . . . . . . . . . V . . P R . . . . . . . . . . . . . . . . . . . . . . . . .
             - - D . V S . . . . . . . . . . S . . . . . . . . . . . . . V . . P R . . . . . . . . . . . . . . . . . . . . . . . . .

120           130           140           150           160           170
                       *             *             *             *             *             *
             L H L V P S G I L N E D T T C V I G N G V V V H L P G L F K E I D G L E S N G V S C K G R I L V S D R A H L L F D F H Q
             . . . . . . . . . H . G . L . . V . . . A . I . V . . F . G . . . . . . . . . . R . G . . . . . . . . . . . . . . . L . .
             . . . . . . . . . H . G . L . . V . . . A . I . V . . F . G . . . . . Q . . . . . . D . . . . . . . . . . . . . . . L . .

180           190           200           210           220           230
                       *             *             *             *             *             *
             E V D G L R E S E L A K S F I G T T K R G I G P A Y S S K V I R N G I R V G D L R H M D T L P Q K L D L L L S D A A A R
             A . . . . . . A . . E N . . . . . . . . . . . . . C . . . . . T . . . L . . C . . . . . . . F G D . . . I . F K . . . S .
             T . . . . . . A . . . N . . . . . . . . . . . . . C . . . . . T . . . L . . C . . . . . . . F G D . . . V . F E . . . . .

240           250           260           270           280           290
                       *             *             *             *             *             *
             F Q G F K Y T P E M L R E E V E A Y K R Y A D R L E P Y I T D T V H F I N D S I S Q K K K V L V E G G Q A T M L D I D F
             . . . . Q . S K S L . K . . . . R . . K F . . . . . . F . A . . . . V L . E . . K . . . . I . . . . . . . . . . . . . . .
             . E . . . . S K G . . K . . . . R . . . F . E . . . . F . A . . . . V L . E . . R . . . . I . . . . . . . . . . . . . . .

300           310           320           330           340           350
                       *             *             *             *             *             *
             G T Y P F V T S S S P S A G G I C T G L G I A P S V V G D L I G V V K A Y T T R V G S G P F P T E N L G T G G D L L R L
             . . . . . . . . . . . . . . . . . R A I . . . . . . . . . . . . S . . . . . . . . . L F . E E . . R . . K
             . . . . . . . . . . . . . . . . . R . I . . . . . . . . . . . . . . . . . . . . . . L . . E E . . V . . K 360           370           380           390           400           410
                       *             *             *             *             *             *
             A G Q E F G T T T G R P R R C G W L D I V A L K F S C Q I N G F A S L N L T K L D V L S D L N E I Q L G V A Y K R S D G
             . . M . . . . . . . . . . . . . . . . . . . H . . . . . . . . . S . . . . . . . . . . . . . G . S . . K V . . S . T Q T . .
             . . M . . . . . . . . . . . . . . . . . . Y C . D . . . . S . . . . . . . . . . . . . . . . G . P . . K . . . S . N Q M . .

420           430           440           450           460           470
                       *             *             *             *             *             *
             T P V K S F P G D L R L L E E L H V E Y E V L P G W K S D I S S V R N Y S D L P K A A Q Q Y V E R I E E L V G V P I H Y
             Q K L Q . . . . . . D T . . Q V Q . N . . . . . . . Q . . . . . . R . D E . . Q . . R L . . . . . . . . . . . . V . .
             E K L Q . . . . . . D T . . Q V Q . N . . . . . . . D . . . . . . . S . . E . . Q . . R R . . . . . . . . A . . . V . .

480           490
                       *             *
             I GI G P G R D A L I Y K
             . . V . . . . . . . . . .
             . . V . . . . . . . . . .
```

TABLE 2

Comparison of the Arabidopsis (SEQ ID NO:1) Maize (SEQ ID NO:3) and
Wheat (SEQ ID NO:5) S-1 Nucleic Acid Sequences in the Coding Region
Identical residues are denoted by a period. Gaps in the alignment are indicated by a dash.

```
                      40            50            60            70            80            90
                       *             *             *             *             *             *
Arabidopsis  ATGTCTCTCTCTTCCCTCACTCTCGACTCCAATCCAAGATTCGCTGTTGGTGGACCTTAT
Maize        . . . . . G . . . . . CA. A. . . . GC. A. CCGG. . GCCG. - - - - - - - . . . C. CC. - - . . . G. GG. A
Wheat        - - - - - - - - - - - - - - - - - GC. G. CGC. . C. G. . - - - - - - - - - - - - G. GC. GG. . A. . T. . . . C.

100           110           120           130           140           150
                       *             *             *             *             *             *
             CACCGCCGTTATCCTCCTCTTCACCACCCTCGAAGCTTCGTCTCTTGCTCTGCTAAACGT
             A. T. C. - - - - . T. T. C. GG. . GGC. . GG. GG. . C. . - . . C. . . ACA. . T. C. CAAGGC. . . G
             . C. . . - - - - - - - - - G. . G. CC. GG. G. . G. . . TC. G. G. . - - - . C. . . C. G. GAG. CA. G
```

TABLE 2-continued

Comparison of the Arabidopsis (SEQ ID NO:1) Maize (SEQ ID NO:3) and
Wheat (SEQ ID NO:5) S-1 Nucleic Acid Sequences in the Coding Region
Identical residues are denoted by a period. Gaps in the alignment are indicated by a dash.

```
              160         170         180         190         200
               *           *           *           *           *
CCAGCT-----GTCTCCGCTTCACTGAGCG---TCGCCGCTGATTCAGCCGCC-ACTGAG
. TCC. .-----. . . C. . . . CG. -------. . ---. . T. . . . C. C. A. T. . G. . T-GT. C. C
. . CC. GCCCCC. C. G. . . . G. . CGC. CT. . CGG. G. AG. . G. . CC. C. . . . . . G. . A. G.

210         220         230         240         250         260
               *           *           *           *           *           *
TCTCTTGGACGGATTGGATCACTGAGTCAAGTATCTGGTGTACTCGGTTGCCAATGGGGA
G. GGAG. ATA. . G. . TCG. . G. . . . C. . . . . . C. . C. . C. . G. . G. . G. CG. . G. . . . . C
. . . . -------------G. . G. . . . . C. . G. . C. . C. . . C. . G. . . . . G. CG. . G. . . . . C 270         280         290         300         310         320
               *           *           *           *           *           *
GATGAAGGTAAAGGCAAACTCGTTGACATCTTAGCCCAACACTTTGACATCGTTGCTCGT
. . C. . G. . A. . G. . . . . G. . . . . C. . . G. GC. C. . . . CC. G. . . C. . . . . A. . C. . G. . .
. . C. . G. . G. . G. . G. . G. . . . . C. . . G. GC. C. . . . CC. G. . . C. . . . . . . . . C. . G. . .

330         340         350         360         370         380
               *           *           *           *           *           *
TGTCAGGGTGGAGCTAATGCTGGACACACTATATACAATTCAGAGGGAAAGAAATTTGCA
. . C. . . . . G. . . . . G. . C. . . . . . . . . T. . C. . C. . . . . C. . . . . A. . C. . . . . G. . . . . T
. . C. . . . . . . . . . A. . . . . . . . . . . . . . . C. . C. . . . . . C. . T. . A. . C. . . . . . . . . . . C 390         400         410         420         430         440
               *           *           *           *           *           *
CTTCACCTTGTGCCTTCAGGTATCCTGAATGAGGATACTACTTGTGTCATTGGAAACGGA
. . G. . T. . . . . T. . A. . T. . . . . T. . CC. . . . A. GG. . ACTG. . . . . TG. . . . C. . T. . .
. . . . . T. . . . . T. . A. . T. . . . . T. . CC. . . . A. GA. . ACTC. . . . . TG. . . . C. . . . . .

450         460         470         480         490         500
               *           *           *           *           *           *
GTTGTGGTGCATTTGCCAGGTCTCTTCAAAGAGATTGATGGTTTGGAGTCCAATGGTGTC
. CA. . CA. C. . . G. T. . . . . GT. . . . TGG. . . A. . . . . . . . . C. T. . . . . . . . . . . A. . .
. CG. . . A. C. . . G. T. . . . . GT. . . . TGGC. . A. . . . . . . . . C. TC. A. . A. . . . . A. . .

510         520         530         540         550         560
               *           *           *           *           *           *
TCCTGTAAAGGAAGGATTTTGGTCTCTGATCGCGCTCACTTGTTATTCGATTTCCATCAA
CG. . . CGGT. . . . . . . . AC. . . . A. . C. . C. . G. . A. . TC. . C. G. . T. . . C. G. . C. . G
AGT. . . G. T. . . . . A. . AC. . . . G. . . . . CA. G. . . . . T. . . C. C. . T. . . C. G. . . . . G 570         580         590         600         610         620
               *           *           *           *           *           *
GAGGTTGATGGGCTCAGGGAATCTGAGCTTGCCAAGTCGTTCATTGGCACCACCAAGAGG
. CT. . G. . . . . A. . T. . . . . . G. A. . . . . . . AA. . T. . A. . T. . A. . G. . A. . T. . . . . A
ACT. . A. . . . . A. . T. . . . . . G. C. . . . . . . . . A. . T. . C. . . . . A. . A. . G. . T. . . . . A 630         640         650         660         670         680
               *           *           *           *           *           *
GGAATTGGTCCTGCCTACTCTAGTAAAGTGATAAGGAATGGTATTAGAGTAGGTGATCTC
. . C. . . . . . . . . . TGT. . . . . C. . C. . G. . A. CTC. A. . . . . AC. GC. G. . TT. . . . . T. A
. . C. . . . . A. . . TGT. . T. . C. . C. . G. . C. CTC. A. . . . . GC. GC. . . . TT. . . . . . . A 690         700         710         720         730         740
               *           *           *           *           *           *
AGGCACATGGATACTTTACCTCAAAAGCTTGACCTTTTACTATCAGATGCAGCGGCAAGG
C. A. . . . . . . . . C. . . . . TGGGG. T. . . . . . . . . A. C. . . T. CAA. . . C. . T. . TT. G. . A
. . . . . . . . . . . C. . . . . TGGGG. T. . . . . . . . TG. . . . . T. CGA. . . C. . T. . T. . G. . .

750         760         770         780         790         800
               *           *           *           *           *           *
TTTCAAGGGTTCAAGTATACTCCTGAAATGCTTCGGGAAGAAGTTGAAGCATACAAGAGA
. . . . . . . . . C. . TC. . . . C. GCAAAAGCT. . . . CAA. . . . . . . G. . . . . GAG. . . . . . . . AG
. . . G. . . . C. . . . . . . . . C. GCAAA. GC. . . . . CAA. . . . . . . G. . . . . GAGG. . . . . . . . G 810         820         830         840         850         860
               *           *           *           *           *           *
TACGCTGACAGATTGGAGCCCTACATTACTGACACTGTCCATTTCATCAATGACTCGATT
. TT. . . . . TC. C. . . . . . . . . . T. . . . G. . . . T. . C. . G. . . G. GC. A. . . . . A. . T. . C
. TT. . A. . GC. T. . . . . . . . . . T. . . . G. . . . . . . . . . T. . . G. GT. G. . . . . A. . C. . C
```

TABLE 2-continued

Comparison of the Arabidopsis (SEQ ID NO:1) Maize (SEQ ID NO:3) and
Wheat (SEQ ID NO:5) S-1 Nucleic Acid Sequences in the Coding Region
Identical residues are denoted by a period. Gaps in the alignment are indicated by a dash.

```
        870         880         890         900         910         920
         *           *           *           *           *           *
TCGCAGAAGAAAAAGGTTTTGGTCGAAGGTGGTCAAGCTACAATGTTGGACATTGACTTT
AA........G..AA.CC..........C..C.....A..T...C....T.....T..
CGA.......G..AA..C....T............G..A..T...C....T..C..T...

930         940         950         960         970         980
         *           *           *           *           *           *
GGGACTTATCCTTTTGTTACTTCCTCCAGCCCCTCAGCCGGTGGGATCTGCACAGGTCTT
..C........A.....G.....T..T.....T.....T..C.....A........C..A
..A........A.....G.....T..T.....T..C..T.....A..T.....T..C...

990        1000        1010        1020        1030        1040
         *           *           *           *           *           *
GGTATTGCACCAAGTGTTGTTGGTGATCTAATTGGAGTGGTAAAAGCATACACTACAAGA
..G.....T.....G.CAA....C..C..G............C.....T.....AT.T...
..G.....C..T..G...A....C..C..G........T........T.....A.....G 1050        1060        1070        1080        1090        1100
         *           *           *           *           *           *
GTTGGTTCAGGTCCATTCCCGACAGAAAATTTGGGCACAGGTGGTGACCTTCTTAGGTTA
..C..C..T..C..T.....A..T...CTA..T..AGAG.AA.....T.GC......AA.
.....C..T..C..T.....A..T...CTGC.T..AGAG.AA.....TG........AAG 1110        1120        1130        1140        1150        1160
         *           *           *           *           *           *
GCTGGACAGGAGTTTGGCACTACAACTGGTCGTCCTCGTCGGTGTGGCTGGCTTGACATT
......AT...A........A.....A.....C..AA.G..T..C................
..C...AT...A.....A..G..T..A.....C..AA.A..T..................C 1170        1180        1190        1200        1210        1220
         *           *           *           *           *           *
GTTGCCCTGAAATTTTCTTGCCAAATCAATGGATTTGCATCACTTAATCTCACTAAGCTT
.....G..T..GCACAGC..............G..CT.............G..C..A..G
.....A.......AC.GC..TG.C........G...T.C..T..A.....A..A..A...

1230        1240        1250        1260        1270        1280
         *           *           *           *           *           *
GATGTACTTTCGGATCTGAACGAAATCCAGCTGGGTGTGGCTTACAAGAGGAGTGACGGC
.....T..G..C.GGT..TCA.....TA..G.......TT....T.CCCA..C...T..A
.....T..G..C.GGT.ACCA.....TA..........TT....T..TCAA.TG..T..A 1290        1300        1310        1320        1330        1340
         *           *           *           *           *           *
ACCCCTGTTAAATCATTCCCTGGTGATCTTCGTCTTCTCGAAGAACTGCATGTGGAGTAT
CAGAAGC.GC....C........G......GA.ACC..T..GC..G.A..G..CA.C...
GAGAAAC.AC....C.....A..G......GACACC..G..GC..G.A..G..CA.C...

1350        1360        1370        1380        1390        1400
         *           *           *           *           *           *
GAAGTCTTACCTGGGTGGAAGTCTGACATATCCTCGGTCAGAAACTACTCTGATCTTCCA
..G..TC.G.........C.AAG......T..T..T..TC...GA...GA...A.....C
..G..GC.T.........G.CAG.........T..T...C...GT...AG...A..C..C 1410        1420        1430        1440        1450        1460
         *           *           *           *           *           *
AAGGCTGCTCAGCAATATGTTGAGAGGATTGAAGAACTCGTGGGTGTGCCCATTCATTAC
C.A.....C.GC.TC.....G........A........T..T.....T...G.G..C...
C.A.....C.GC.GT..C..G........A.....G....CC.....T..AG.C..C...

1470        1480        1490        1500
         *           *           *           *
ATTGGTATTGGGCCCGGTCGTGATGCCCTTATATATAAATGA
......G....A..T..CA.A.....T..C.....C..G.A.
......G.C.....T..GA.G....T..G.....C..G.A.
```

Various modifications of the invention described herein will become apparent to those skilled in the art. Such modifications are intended to fall within the scope of the appended claims.

We claim:

1. An isolated DNA molecule encoding a plant adenylosuccinate synthetase(ADSS) protein.

2. The isolated DNA molecule of claim 1, wherein said plant is a dicotyledon.

3. The isolated DNA molecule of claim 2, wherein said dicotyledon is an Arabidopsis species.

4. The isolated DNA molecule of claim 1, wherein said plant is a monocotyledon.

5. The isolated DNA molecule of claim 4, wherein said monocotyledon is selected from the group consisting of maize and wheat.

6. The isolated DNA molecule of claim 5, wherein said monocotyledon is maize.

7. The isolated DNA molecule of claim 5, wherein said monocotyledon is wheat.

8. The isolated DNA molecule of claim 7, wherein said protein comprises the amino acid sequence set forth in SEQ ID NO: 6.

9. The isolated DNA molecule of claim 8 comprising the sequence set forth in SEQ ID NO: 5.

10. An expression cassette comprising a promoter operably linked to the DNA molecule of claim 1.

11. A recombinant vector comprising the expression cassette of claim 10, wherein said vector is capable of being stably transformed into a host cell.

12. A host cell stably transformed with the vector of claim 11, wherein said host cell is capable of expressing said DNA molecule.

13. A host cell of claim 12 selected from the group consisting of a bacterial cell, a yeast cell, and an insect cell.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1516 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 1..1470
        ( D ) OTHER INFORMATION: /product="Arabidopsis Adenylosuccinate Synthetase"

( x i ) SEQUENCE DESCRIPTION: SEQ ID NO:1:

```
ATG  TCT  CTC  TCT  TCC  CTC  ACT  CTC  GAC  TCC  AAT  CCA  AGA  TTC  GCT  GTT        48
Met  Ser  Leu  Ser  Ser  Leu  Thr  Leu  Asp  Ser  Asn  Pro  Arg  Phe  Ala  Val
 1             5                        10                       15

GGT  GGA  CCT  TAT  CAC  CGC  CGT  TAT  CCT  CCT  CTT  CAC  CAC  CCT  CGA  AGC        96
Gly  Gly  Pro  Tyr  His  Arg  Arg  Tyr  Pro  Pro  Leu  His  His  Pro  Arg  Ser
               20                       25                       30

TTC  GTC  TCT  TGC  TCT  GCT  AAA  CGT  CCA  GCT  GTC  TCC  GCT  TCA  CTG  AGC       144
Phe  Val  Ser  Cys  Ser  Ala  Lys  Arg  Pro  Ala  Val  Ser  Ala  Ser  Leu  Ser
          35                       40                       45

GTC  GCC  GCT  GAT  TCA  GCC  GCC  ACT  GAG  TCT  CTT  GGA  CGG  ATT  GGA  TCA       192
Val  Ala  Ala  Asp  Ser  Ala  Ala  Thr  Glu  Ser  Leu  Gly  Arg  Ile  Gly  Ser
     50                       55                       60

CTG  AGT  CAA  GTA  TCT  GGT  GTA  CTC  GGT  TGC  CAA  TGG  GGA  GAT  GAA  GGT       240
Leu  Ser  Gln  Val  Ser  Gly  Val  Leu  Gly  Cys  Gln  Trp  Gly  Asp  Glu  Gly
65                       70                       75                       80

AAA  GGC  AAA  CTC  GTT  GAC  ATC  TTA  GCC  CAA  CAC  TTT  GAC  ATC  GTT  GCT       288
Lys  Gly  Lys  Leu  Val  Asp  Ile  Leu  Ala  Gln  His  Phe  Asp  Ile  Val  Ala
                    85                       90                       95

CGT  TGT  CAG  GGT  GGA  GCT  AAT  GCT  GGA  CAC  ACT  ATA  TAC  AAT  TCA  GAG       336
Arg  Cys  Gln  Gly  Gly  Ala  Asn  Ala  Gly  His  Thr  Ile  Tyr  Asn  Ser  Glu
               100                      105                      110

GGA  AAG  AAA  TTT  GCA  CTT  CAC  CTT  GTG  CCT  TCA  GGT  ATC  CTG  AAT  GAG       384
Gly  Lys  Lys  Phe  Ala  Leu  His  Leu  Val  Pro  Ser  Gly  Ile  Leu  Asn  Glu
          115                      120                      125

GAT  ACT  ACT  TGT  GTC  ATT  GGA  AAC  GGA  GTT  GTG  GTG  CAT  TTG  CCA  GGT       432
Asp  Thr  Thr  Cys  Val  Ile  Gly  Asn  Gly  Val  Val  Val  His  Leu  Pro  Gly
     130                      135                      140

CTC  TTC  AAA  GAG  ATT  GAT  GGT  TTG  GAG  TCC  AAT  GGT  GTC  TCC  TGT  AAA       480
Leu  Phe  Lys  Glu  Ile  Asp  Gly  Leu  Glu  Ser  Asn  Gly  Val  Ser  Cys  Lys
145                      150                      155                      160

GGA  AGG  ATT  TTG  GTC  TCT  GAT  CGC  GCT  CAC  TTG  TTA  TTC  GAT  TTC  CAT       528
Gly  Arg  Ile  Leu  Val  Ser  Asp  Arg  Ala  His  Leu  Leu  Phe  Asp  Phe  His
                    165                      170                      175

CAA  GAG  GTT  GAT  GGG  CTC  AGG  GAA  TCT  GAG  CTT  GCC  AAG  TCG  TTC  ATT       576
Gln  Glu  Val  Asp  Gly  Leu  Arg  Glu  Ser  Glu  Leu  Ala  Lys  Ser  Phe  Ile
               180                      185                      190

GGC  ACC  ACC  AAG  AGG  GGA  ATT  GGT  CCT  GCC  TAC  TCT  AGT  AAA  GTG  ATA       624
Gly  Thr  Thr  Lys  Arg  Gly  Ile  Gly  Pro  Ala  Tyr  Ser  Ser  Lys  Val  Ile
          195                      200                      205
```

```
AGG AAT GGT ATT AGA GTA GGT GAT CTC AGG CAC ATG GAT ACT TTA CCT                672
Arg Asn Gly Ile Arg Val Gly Asp Leu Arg His Met Asp Thr Leu Pro
    210             215                 220

CAA AAG CTT GAC CTT TTA CTA TCA GAT GCA GCG GCA AGG TTT CAA GGG                720
Gln Lys Leu Asp Leu Leu Leu Ser Asp Ala Ala Ala Arg Phe Gln Gly
225             230                 235                 240

TTC AAG TAT ACT CCT GAA ATG CTT CGG GAA GAA GTT GAA GCA TAC AAG                768
Phe Lys Tyr Thr Pro Glu Met Leu Arg Glu Glu Val Glu Ala Tyr Lys
                245                 250                 255

AGA TAC GCT GAC AGA TTG GAG CCC TAC ATT ACT GAC ACT GTC CAT TTC                816
Arg Tyr Ala Asp Arg Leu Glu Pro Tyr Ile Thr Asp Thr Val His Phe
            260                 265                 270

ATC AAT GAC TCG ATT TCG CAG AAG AAA AAG GTT TTG GTC GAA GGT GGT                864
Ile Asn Asp Ser Ile Ser Gln Lys Lys Lys Val Leu Val Glu Gly Gly
        275                 280                 285

CAA GCT ACA ATG TTG GAC ATT GAC TTT GGG ACT TAT CCT TTT GTT ACT                912
Gln Ala Thr Met Leu Asp Ile Asp Phe Gly Thr Tyr Pro Phe Val Thr
    290                 295                 300

TCC TCC AGC CCC TCA GCC GGT GGG ATC TGC ACA GGT CTT GGT ATT GCA                960
Ser Ser Ser Pro Ser Ala Gly Gly Ile Cys Thr Gly Leu Gly Ile Ala
305             310                 315                 320

CCA AGT GTT GTT GGT GAT CTA ATT GGA GTG GTA AAA GCA TAC ACT ACA               1008
Pro Ser Val Val Gly Asp Leu Ile Gly Val Val Lys Ala Tyr Thr Thr
                325                 330                 335

AGA GTT GGT TCA GGT CCA TTC CCG ACA GAA AAT TTG GGC ACA GGT GGT               1056
Arg Val Gly Ser Gly Pro Phe Pro Thr Glu Asn Leu Gly Thr Gly Gly
            340                 345                 350

GAC CTT CTT AGG TTA GCT GGA CAG GAG TTT GGC ACT ACA ACT GGT CGT               1104
Asp Leu Leu Arg Leu Ala Gly Gln Glu Phe Gly Thr Thr Thr Gly Arg
        355                 360                 365

CCT CGT CGG TGT GGC TGG CTT GAC ATT GTT GCC CTG AAA TTT TCT TGC               1152
Pro Arg Arg Cys Gly Trp Leu Asp Ile Val Ala Leu Lys Phe Ser Cys
    370                 375                 380

CAA ATC AAT GGA TTT GCA TCA CTT AAT CTC ACT AAG CTT GAT GTA CTT               1200
Gln Ile Asn Gly Phe Ala Ser Leu Asn Leu Thr Lys Leu Asp Val Leu
385             390                 395                 400

TCG GAT CTG AAC GAA ATC CAG CTG GGT GTG GCT TAC AAG AGG AGT GAC               1248
Ser Asp Leu Asn Glu Ile Gln Leu Gly Val Ala Tyr Lys Arg Ser Asp
                405                 410                 415

GGC ACC CCT GTT AAA TCA TTC CCT GGT GAT CTT CGT CTT CTC GAA GAA               1296
Gly Thr Pro Val Lys Ser Phe Pro Gly Asp Leu Arg Leu Leu Glu Glu
            420                 425                 430

CTG CAT GTG GAG TAT GAA GTC TTA CCT GGG TGG AAG TCT GAC ATA TCC               1344
Leu His Val Glu Tyr Glu Val Leu Pro Gly Trp Lys Ser Asp Ile Ser
        435                 440                 445

TCG GTC AGA AAC TAC TCT GAT CTT CCA AAG GCT GCT CAG CAA TAT GTT               1392
Ser Val Arg Asn Tyr Ser Asp Leu Pro Lys Ala Ala Gln Gln Tyr Val
    450                 455                 460

GAG AGG ATT GAA GAA CTC GTG GGT GTG CCC ATT CAT TAC ATT GGT ATT               1440
Glu Arg Ile Glu Glu Leu Val Gly Val Pro Ile His Tyr Ile Gly Ile
465             470                 475                 480

GGG CCC GGT CGT GAT GCC CTT ATA TAT AAA TGATTTTAG TGTTAGGCTT                   1490
Gly Pro Gly Arg Asp Ala Leu Ile Tyr Lys
                485                 490

TTTTGGTTCC TCCACAAACT CAAAAT                                                   1516

( 2 ) INFORMATION FOR SEQ ID NO:2:

( i ) SEQUENCE CHARACTERISTICS:
          ( A ) LENGTH: 490 amino acids
          ( B ) TYPE: amino acid
```

( D ) TOPOLOGY: linear ( i i ) MOLECULE TYPE: protein ( x i ) SEQUENCE DESCRIPTION: SEQ ID NO:2:

```
Met  Ser  Leu  Ser  Ser  Leu  Thr  Leu  Asp  Ser  Asn  Pro  Arg  Phe  Ala  Val
  1              5                        10                       15

Gly  Gly  Pro  Tyr  His  Arg  Arg  Tyr  Pro  Pro  Leu  His  His  Pro  Arg  Ser
              20                       25                       30

Phe  Val  Ser  Cys  Ser  Ala  Lys  Arg  Pro  Ala  Val  Ser  Ala  Ser  Leu  Ser
         35                       40                       45

Val  Ala  Ala  Asp  Ser  Ala  Ala  Thr  Glu  Ser  Leu  Gly  Arg  Ile  Gly  Ser
    50                       55                       60

Leu  Ser  Gln  Val  Ser  Gly  Val  Leu  Gly  Cys  Gln  Trp  Gly  Asp  Glu  Gly
 65                       70                       75                       80

Lys  Gly  Lys  Leu  Val  Asp  Ile  Leu  Ala  Gln  His  Phe  Asp  Ile  Val  Ala
                   85                       90                       95

Arg  Cys  Gln  Gly  Gly  Ala  Asn  Ala  Gly  His  Thr  Ile  Tyr  Asn  Ser  Glu
              100                      105                      110

Gly  Lys  Lys  Phe  Ala  Leu  His  Leu  Val  Pro  Ser  Gly  Ile  Leu  Asn  Glu
              115                      120                      125

Asp  Thr  Thr  Cys  Val  Ile  Gly  Asn  Gly  Val  Val  Val  His  Leu  Pro  Gly
    130                      135                      140

Leu  Phe  Lys  Glu  Ile  Asp  Gly  Leu  Glu  Ser  Asn  Gly  Val  Ser  Cys  Lys
145                      150                      155                      160

Gly  Arg  Ile  Leu  Val  Ser  Asp  Arg  Ala  His  Leu  Leu  Phe  Asp  Phe  His
                   165                      170                      175

Gln  Glu  Val  Asp  Gly  Leu  Arg  Glu  Ser  Glu  Leu  Ala  Lys  Ser  Phe  Ile
              180                      185                      190

Gly  Thr  Thr  Lys  Arg  Gly  Ile  Gly  Pro  Ala  Tyr  Ser  Ser  Lys  Val  Ile
         195                      200                      205

Arg  Asn  Gly  Ile  Arg  Val  Gly  Asp  Leu  Arg  His  Met  Asp  Thr  Leu  Pro
    210                      215                      220

Gln  Lys  Leu  Asp  Leu  Leu  Ser  Asp  Ala  Ala  Ala  Arg  Phe  Gln  Gly
225                      230                      235                      240

Phe  Lys  Tyr  Thr  Pro  Glu  Met  Leu  Arg  Glu  Glu  Val  Glu  Ala  Tyr  Lys
              245                      250                      255

Arg  Tyr  Ala  Asp  Arg  Leu  Glu  Pro  Tyr  Ile  Thr  Asp  Thr  Val  His  Phe
              260                      265                      270

Ile  Asn  Asp  Ser  Ile  Ser  Gln  Lys  Lys  Val  Leu  Val  Glu  Gly  Gly
              275                      280                      285

Gln  Ala  Thr  Met  Leu  Asp  Ile  Asp  Phe  Gly  Thr  Tyr  Pro  Phe  Val  Thr
    290                      295                      300

Ser  Ser  Ser  Pro  Ser  Ala  Gly  Gly  Ile  Cys  Thr  Gly  Leu  Gly  Ile  Ala
305                      310                      315                      320

Pro  Ser  Val  Val  Gly  Asp  Leu  Ile  Gly  Val  Lys  Ala  Tyr  Thr  Thr
              325                      330                      335

Arg  Val  Gly  Ser  Gly  Pro  Phe  Pro  Thr  Glu  Asn  Leu  Gly  Thr  Gly  Gly
              340                      345                      350

Asp  Leu  Leu  Arg  Leu  Ala  Gly  Gln  Glu  Phe  Gly  Thr  Thr  Thr  Gly  Arg
              355                      360                      365

Pro  Arg  Arg  Cys  Gly  Trp  Leu  Asp  Ile  Val  Ala  Leu  Lys  Phe  Ser  Cys
    370                      375                      380

Gln  Ile  Asn  Gly  Phe  Ala  Ser  Leu  Asn  Leu  Thr  Lys  Leu  Asp  Val  Leu
385                      390                      395                      400
```

```
Ser Asp Leu Asn Glu Ile Gln Leu Gly Val Ala Tyr Lys Arg Ser Asp
                405                 410                 415

Gly Thr Pro Val Lys Ser Phe Pro Gly Asp Leu Arg Leu Leu Glu Glu
            420                 425                 430

Leu His Val Glu Tyr Glu Val Leu Pro Gly Trp Lys Ser Asp Ile Ser
            435                 440                 445

Ser Val Arg Asn Tyr Ser Asp Leu Pro Lys Ala Ala Gln Gln Tyr Val
    450                 455                 460

Glu Arg Ile Glu Glu Leu Val Gly Val Pro Ile His Tyr Ile Gly Ile
465                 470                 475                 480

Gly Pro Gly Arg Asp Ala Leu Ile Tyr Lys
                485                 490
```

( 2 ) INFORMATION FOR SEQ ID NO:3:

( i ) SEQUENCE CHARACTERISTICS:
        ( A ) LENGTH: 1835 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 18..1469
        ( D ) OTHER INFORMATION: /product="Maize Adenylosuccinate
            Synthetase"

( x i ) SEQUENCE DESCRIPTION: SEQ ID NO:3:

```
AAAACCCTCC CACCATC ATG TCG CTC TCC ACA CTC AGC CAC CCG GCC GCC       50
                   Met Ser Leu Ser Thr Leu Ser His Pro Ala Ala
                                   495                 500

GCC GCC GCC GGG AGC GGA AAA TCC CTT TTC CCG GCT GGC CCG GCG GCG      98
Ala Ala Ala Gly Ser Gly Lys Ser Leu Phe Pro Ala Gly Pro Ala Ala
                505                 510                 515

CAG TCC GTA CAT TTC CCC AAG GCA CGG CTC CCT GTC CCC GCC GCC GTC     146
Gln Ser Val His Phe Pro Lys Ala Arg Leu Pro Val Pro Ala Ala Val
            520                 525                 530

TCC GCC GCT ACT GCG GCT GTT CAC GCG GAG GAT AGG GTT TCG TCG CTG     194
Ser Ala Ala Thr Ala Ala Val His Ala Glu Asp Arg Val Ser Ser Leu
    535                 540                 545

ACT CAA GTC TCC GGC GTG CTG GGG TCG CAG TGG GGC GAC GAG GGA AAG     242
Thr Gln Val Ser Gly Val Leu Gly Ser Gln Trp Gly Asp Glu Gly Lys
550                 555                 560                 565

GGC AAG CTC GTC GAC GTG CTC GCC CCC CGC TTC GAC ATA GTC GCG CGT     290
Gly Lys Leu Val Asp Val Leu Ala Pro Arg Phe Asp Ile Val Ala Arg
                570                 575                 580

TGC CAG GGG GGA GCG AAC GCT GGA CAT ACC ATC TAC AAC TCA GAA GGC     338
Cys Gln Gly Gly Ala Asn Ala Gly His Thr Ile Tyr Asn Ser Glu Gly
                585                 590                 595

AAG AAG TTT GCT CTG CAT CTT GTT CCA TCT GGT ATT CTC CAT GAA GGG     386
Lys Lys Phe Ala Leu His Leu Val Pro Ser Gly Ile Leu His Glu Gly
            600                 605                 610

ACA CTG TGT GTT GTT GGC AAT GGA GCA GTC ATC CAT GTT CCA GGG TTC     434
Thr Leu Cys Val Val Gly Asn Gly Ala Val Ile His Val Pro Gly Phe
    615                 620                 625

TTT GGA GAA ATT GAT GGT CTT GAG TCC AAT GGA GTC CGC TGC GGT GGA     482
Phe Gly Glu Ile Asp Gly Leu Glu Ser Asn Gly Val Arg Cys Gly Gly
630                 635                 640                 645
```

```
AGG ATA CTG GTA TCC GAC CGG GCA CAT CTG CTG TTT GAT CTG CAC CAG     530
Arg Ile Leu Val Ser Asp Arg Ala His Leu Leu Phe Asp Leu His Gln
            650                 655                 660

GCT GTG GAT GGA CTT AGG GAA GCA GAG CTT GAA AAT TCA TTT ATA GGG     578
Ala Val Asp Gly Leu Arg Glu Ala Glu Leu Glu Asn Ser Phe Ile Gly
                665                 670                 675

ACA ACT AAG AGA GGC ATT GGT CCT TGT TAC TCC AGC AAG GTA ACT CGA     626
Thr Thr Lys Arg Gly Ile Gly Pro Cys Tyr Ser Ser Lys Val Thr Arg
            680                 685                 690

AAT GGA CTG CGG GTT TGT GAT TTA CGA CAC ATG GAC ACT TTT GGG GAT     674
Asn Gly Leu Arg Val Cys Asp Leu Arg His Met Asp Thr Phe Gly Asp
        695                 700                 705

AAG CTT GAC ATC TTA TTC AAA GAC GCT GCT TCG AGA TTT CAA GGC TTT     722
Lys Leu Asp Ile Leu Phe Lys Asp Ala Ala Ser Arg Phe Gln Gly Phe
710                 715                 720                 725

CAG TAC AGC AAA AGC TTG CTC AAG GAA GAG GTT GAG AGA TAC AAG AAG     770
Gln Tyr Ser Lys Ser Leu Leu Lys Glu Glu Val Glu Arg Tyr Lys Lys
                730                 735                 740

TTT GCT GAT CGC TTG GAG CCC TTC ATT GCT GAT ACC GTG CAT GTG CTA     818
Phe Ala Asp Arg Leu Glu Pro Phe Ile Ala Asp Thr Val His Val Leu
            745                 750                 755

AAT GAA TCT ATC AAG CAG AAG AAG AAA ATC CTG GTC GAA GGC GGC CAA     866
Asn Glu Ser Ile Lys Gln Lys Lys Lys Ile Leu Val Glu Gly Gly Gln
        760                 765                 770

GCA ACT ATG CTG GAT ATT GAT TTT GGC ACT TAT CCA TTT GTG ACT TCT     914
Ala Thr Met Leu Asp Ile Asp Phe Gly Thr Tyr Pro Phe Val Thr Ser
775                 780                 785

TCT AGC CCT TCA GCT GGC GGG ATA TGC ACA GGC CTA GGG ATT GCT CCA     962
Ser Ser Pro Ser Ala Gly Gly Ile Cys Thr Gly Leu Gly Ile Ala Pro
790                 795                 800                 805

AGG GCA ATT GGC GAC CTG ATT GGA GTG GTC AAA GCT TAC ACA TCT AGA    1010
Arg Ala Ile Gly Asp Leu Ile Gly Val Val Lys Ala Tyr Thr Ser Arg
                810                 815                 820

GTC GGC TCT GGC CCT TTC CCA ACT GAA CTA TTT GGA GAG GAA GGT GAT    1058
Val Gly Ser Gly Pro Phe Pro Thr Glu Leu Phe Gly Glu Glu Gly Asp
            825                 830                 835

CGC CTT AGG AAA GCT GGA ATG GAA TTT GGC ACA ACA ACA GGT CGC CCA    1106
Arg Leu Arg Lys Ala Gly Met Glu Phe Gly Thr Thr Thr Gly Arg Pro
        840                 845                 850

AGG CGT TGC GGC TGG CTT GAC ATT GTT GCG CTT AAG CAC AGC TGC CAA    1154
Arg Arg Cys Gly Trp Leu Asp Ile Val Ala Leu Lys His Ser Cys Gln
855                 860                 865

ATC AAT GGG TTC TCA TCA CTT AAT CTG ACC AAA CTG GAT GTT CTG TCC    1202
Ile Asn Gly Phe Ser Ser Leu Asn Leu Thr Lys Leu Asp Val Leu Ser
870                 875                 880                 885

GGG TTG TCA GAA ATT AAG GTG GGT GTT TCT TAT ACC CAG ACT GAT GGA    1250
Gly Leu Ser Glu Ile Lys Val Gly Val Ser Tyr Thr Gln Thr Asp Gly
                890                 895                 900

CAG AAG CTG CAA TCC TTC CCT GGG GAT CTT GAT ACC CTT GAG CAA GTA    1298
Gln Lys Leu Gln Ser Phe Pro Gly Asp Leu Asp Thr Leu Glu Gln Val
            905                 910                 915

CAG GTC AAC TAT GAG GTT CTG CCT GGG TGG CAA AGT GAC ATT TCT TCT    1346
Gln Val Asn Tyr Glu Val Leu Pro Gly Trp Gln Ser Asp Ile Ser Ser
        920                 925                 930

GTT CGA AGA TAC GAT GAA CTT CCC CAA GCT GCC CGC CTC TAT GTG GAG    1394
Val Arg Arg Tyr Asp Glu Leu Pro Gln Ala Ala Arg Leu Tyr Val Glu
935                 940                 945

AGG ATA GAA GAA CTT GTT GGT GTT CCC GTG CAC TAC ATT GGT GTT GGA    1442
Arg Ile Glu Glu Leu Val Gly Val Pro Val His Tyr Ile Gly Val Gly
950                 955                 960                 965
```

```
CCT GGC AGA GAT GCT CTC ATA TAC AAG  TAAAAGCAAC TTTATTTGGT           1489
Pro Gly Arg Asp Ala Leu Ile Tyr Lys
                            970

CCTTGGTTGG GCGGAAACCT GGCCGGGACT CGGGAGCATT TGCATTTTCT TGGCGTGGTA    1549

GCTTTGATA CGGTGAAGTC ACTGACTCGT GGAGTGATGT TGCTCAATAA TCAGAACCTT     1609

GTTCTAATAC AGCCGCTGAG ACATCAGCTA AGGCGAATAA GGGAAGGATG AGTCATTTGC    1669

ACCATGTTTG ACCACCAATT GTTAGGTGGT CCATATATTT TGTACTAATT GTGAGACTTT    1729

GTGCTATGGA TCTCAACTGT ATACCTTGCT GGTGCATGGC TTTGGGTTTA CATGGTTGAA    1789

AATGAGATTG GTGTACTAAT TGTCTAAAAA AAAAAAAAAA AAAAAA                   1835
```

( 2 ) INFORMATION FOR SEQ ID NO:4:

( i ) SEQUENCE CHARACTERISTICS:
        ( A ) LENGTH: 484 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Ser Leu Ser Thr Leu Ser His Pro Ala Ala Ala Ala Gly Ser
 1               5                  10                  15

Gly Lys Ser Leu Phe Pro Ala Gly Pro Ala Ala Gln Ser Val His Phe
                20                  25                  30

Pro Lys Ala Arg Leu Pro Val Pro Ala Ala Val Ser Ala Ala Thr Ala
            35                  40                  45

Ala Val His Ala Glu Asp Arg Val Ser Ser Leu Thr Gln Val Ser Gly
        50                  55                  60

Val Leu Gly Ser Gln Trp Gly Asp Glu Gly Lys Gly Lys Leu Val Asp
65                  70                  75                  80

Val Leu Ala Pro Arg Phe Asp Ile Val Ala Arg Cys Gln Gly Gly Ala
                85                  90                  95

Asn Ala Gly His Thr Ile Tyr Asn Ser Glu Gly Lys Lys Phe Ala Leu
                100                 105                 110

His Leu Val Pro Ser Gly Ile Leu His Glu Gly Thr Leu Cys Val Val
            115                 120                 125

Gly Asn Gly Ala Val Ile His Val Pro Gly Phe Phe Gly Glu Ile Asp
    130                 135                 140

Gly Leu Glu Ser Asn Gly Val Arg Cys Gly Gly Arg Ile Leu Val Ser
145                 150                 155                 160

Asp Arg Ala His Leu Leu Phe Asp Leu His Gln Ala Val Asp Gly Leu
                165                 170                 175

Arg Glu Ala Glu Leu Glu Asn Ser Phe Ile Gly Thr Thr Lys Arg Gly
            180                 185                 190

Ile Gly Pro Cys Tyr Ser Ser Lys Val Thr Arg Asn Gly Leu Arg Val
        195                 200                 205

Cys Asp Leu Arg His Met Asp Thr Phe Gly Asp Lys Leu Asp Ile Leu
    210                 215                 220

Phe Lys Asp Ala Ala Ser Arg Phe Gln Gly Phe Gln Tyr Ser Lys Ser
225                 230                 235                 240

Leu Leu Lys Glu Glu Val Glu Arg Tyr Lys Lys Phe Ala Asp Arg Leu
                245                 250                 255

Glu Pro Phe Ile Ala Asp Thr Val His Val Leu Asn Glu Ser Ile Lys
            260                 265                 270

Gln Lys Lys Lys Ile Leu Val Glu Gly Gly Gln Ala Thr Met Leu Asp
```

```
                    275                         280                         285
    Ile  Asp  Phe  Gly  Thr  Tyr  Pro  Phe  Val  Thr  Ser  Ser  Ser  Pro  Ser  Ala
         290                       295                    300

Gly  Gly  Ile  Cys  Thr  Gly  Leu  Gly  Ile  Ala  Pro  Arg  Ala  Ile  Gly  Asp
    305                           310                    315                      320

Leu  Ile  Gly  Val  Val  Lys  Ala  Tyr  Thr  Ser  Arg  Val  Gly  Ser  Gly  Pro
                        325                    330                      335

Phe  Pro  Thr  Glu  Leu  Phe  Gly  Glu  Glu  Gly  Asp  Arg  Leu  Arg  Lys  Ala
                   340                         345                      350

Gly  Met  Glu  Phe  Gly  Thr  Thr  Thr  Gly  Arg  Pro  Arg  Arg  Cys  Gly  Trp
              355                         360                       365

Leu  Asp  Ile  Val  Ala  Leu  Lys  His  Ser  Cys  Gln  Ile  Asn  Gly  Phe  Ser
         370                       375                       380

Ser  Leu  Asn  Leu  Thr  Lys  Leu  Asp  Val  Leu  Ser  Gly  Leu  Ser  Glu  Ile
    385                           390                       395                      400

Lys  Val  Gly  Val  Ser  Tyr  Thr  Gln  Thr  Asp  Gly  Gln  Lys  Leu  Gln  Ser
                        405                    410                       415

Phe  Pro  Gly  Asp  Leu  Asp  Thr  Leu  Glu  Gln  Val  Gln  Val  Asn  Tyr  Glu
                   420                          425                         430

Val  Leu  Pro  Gly  Trp  Gln  Ser  Asp  Ile  Ser  Ser  Val  Arg  Arg  Tyr  Asp
              435                         440                       445

Glu  Leu  Pro  Gln  Ala  Ala  Arg  Leu  Tyr  Val  Glu  Arg  Ile  Glu  Glu  Leu
         450                       455                       460

Val  Gly  Val  Pro  Val  His  Tyr  Ile  Gly  Val  Gly  Pro  Gly  Arg  Asp  Ala
    465                      470                       475                        480

Leu  Ile  Tyr  Lys
```

( 2 ) INFORMATION FOR SEQ ID NO:5:

( i ) SEQUENCE CHARACTERISTICS:
        ( A ) LENGTH: 1741 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 1..1428
        ( D ) OTHER INFORMATION: /product="Wheat Adenylosuccinate
        Synthetase"

( x i ) SEQUENCE DESCRIPTION: SEQ ID NO:5:

```
GCC  GCC  GCC  GCC  GCC  GGG  CGG  GGG  AGG  TCC  TTC  TCC  CCG  GCC  GCC  CCG        48
Ala  Ala  Ala  Ala  Ala  Gly  Arg  Gly  Arg  Ser  Phe  Ser  Pro  Ala  Ala  Pro
  1                  5                      10                       15

GCG  CCG  TCG  TCG  GTG  CGC  CTG  CCC  GGG  AGA  CAG  GCC  CCC  GCC  CCC  GCC        96
Ala  Pro  Ser  Ser  Val  Arg  Leu  Pro  Gly  Arg  Gln  Ala  Pro  Ala  Pro  Ala
                   20                      25                      30

GCC  GCG  TCC  GCG  CTC  GCG  GTG  GAG  GCG  GAC  CCC  GCC  GCC  GAC  AGG  GTC       144
Ala  Ala  Ser  Ala  Leu  Ala  Val  Glu  Ala  Asp  Pro  Ala  Ala  Asp  Arg  Val
              35                      40                      45

TCG  TCG  CTG  AGC  CAG  GTC  TCC  GGC  GTG  CTC  GGG  TCG  CAG  TGG  GGC  GAC       192
Ser  Ser  Leu  Ser  Gln  Val  Ser  Gly  Val  Leu  Gly  Ser  Gln  Trp  Gly  Asp
         50                      55                      60

GAG  GGG  AAG  GGG  AAG  CTC  GTC  GAC  GTG  CTC  GCC  CCC  CGC  TTC  GAC  ATC       240
Glu  Gly  Lys  Gly  Lys  Leu  Val  Asp  Val  Leu  Ala  Pro  Arg  Phe  Asp  Ile
 65                      70                      75                       80
```

```
GTC GCG CGT TGC CAG GGT GGA GCA AAT GCT GGA CAC ACC ATC TAC AAC        288
Val Ala Arg Cys Gln Gly Gly Ala Asn Ala Gly His Thr Ile Tyr Asn
             85                  90                  95

TCT GAA GGC AAG AAA TTT GCC CTT CAT CTT GTT CCA TCT GGT ATT CTC        336
Ser Glu Gly Lys Lys Phe Ala Leu His Leu Val Pro Ser Gly Ile Leu
            100                 105                 110

CAT GAA GGA ACA CTC TGT GTT GTT GGC AAC GGA GCG GTG ATC CAT GTT        384
His Glu Gly Thr Leu Cys Val Val Gly Asn Gly Ala Val Ile His Val
            115                 120                 125

CCA GGG TTC TTT GGC GAA ATT GAT GGT CTT CAA TCA AAT GGA GTC AGT        432
Pro Gly Phe Phe Gly Glu Ile Asp Gly Leu Gln Ser Asn Gly Val Ser
            130                 135                 140

TGT GAT GGA AGA ATA CTG GTG TCT GAC AGG GCT CAT TTG CTC TTT GAT        480
Cys Asp Gly Arg Ile Leu Val Ser Asp Arg Ala His Leu Leu Phe Asp
145                 150                 155                 160

CTG CAT CAG ACT GTA GAT GGA CTT AGG GAA GCC GAG CTT GCA AAT TCC        528
Leu His Gln Thr Val Asp Gly Leu Arg Glu Ala Glu Leu Ala Asn Ser
                165                 170                 175

TTC ATA GGA ACG ACT AAG AGA GGC ATT GGA CCT TGT TAT TCC AGC AAG        576
Phe Ile Gly Thr Thr Lys Arg Gly Ile Gly Pro Cys Tyr Ser Ser Lys
            180                 185                 190

GTC ACT CGA AAT GGG CTG CGA GTT TGT GAT CTA AGG CAC ATG GAC ACT        624
Val Thr Arg Asn Gly Leu Arg Val Cys Asp Leu Arg His Met Asp Thr
            195                 200                 205

TTT GGG GAT AAG CTT GAT GTT TTA TTC GAA GAT GCT GCT GCG AGG TTT        672
Phe Gly Asp Lys Leu Asp Val Leu Phe Glu Asp Ala Ala Ala Arg Phe
            210                 215                 220

GAA GGC TTC AAG TAC AGC AAA GGC ATG CTC AAG GAA GAG GTT GAG AGG        720
Glu Gly Phe Lys Tyr Ser Lys Gly Met Leu Lys Glu Glu Val Glu Arg
225                 230                 235                 240

TAC AAG AGG TTT GCA GAG CGT TTG GAG CCC TTC ATT GCT GAC ACT GTT        768
Tyr Lys Arg Phe Ala Glu Arg Leu Glu Pro Phe Ile Ala Asp Thr Val
                245                 250                 255

CAT GTG TTG AAT GAA TCC ATC CGA CAG AAG AAG AAA ATT CTG GTT GAA        816
His Val Leu Asn Glu Ser Ile Arg Gln Lys Lys Lys Ile Leu Val Glu
            260                 265                 270

GGT GGT CAG GCA ACT ATG CTG GAT ATC GAT TTT GGA ACT TAT CCA TTT        864
Gly Gly Gln Ala Thr Met Leu Asp Ile Asp Phe Gly Thr Tyr Pro Phe
            275                 280                 285

GTG ACT TCT TCT AGC CCT TCC GCT GGT GGA ATT TGC ACT GGC CTT GGG        912
Val Thr Ser Ser Ser Pro Ser Ala Gly Gly Ile Cys Thr Gly Leu Gly
290                 295                 300

ATT GCC CCT AGG GTT ATT GGC GAC CTG ATT GGA GTT GTA AAA GCT TAC        960
Ile Ala Pro Arg Val Ile Gly Asp Leu Ile Gly Val Val Lys Ala Tyr
305                 310                 315                 320

ACA ACA AGG GTT GGC TCT GGC CCT TTC CCA ACT GAA CTG CTT GGA GAG        1008
Thr Thr Arg Val Gly Ser Gly Pro Phe Pro Thr Glu Leu Leu Gly Glu
                325                 330                 335

GAA GGT GAT GTT CTT AGG AAG GCC GGA ATG GAA TTT GGA ACG ACT ACA        1056
Glu Gly Asp Val Leu Arg Lys Ala Gly Met Glu Phe Gly Thr Thr Thr
            340                 345                 350

GGT CGC CCA AGA CGT TGT GGC TGG CTT GAC ATC GTT GCA CTG AAA TAC        1104
Gly Arg Pro Arg Arg Cys Gly Trp Leu Asp Ile Val Ala Leu Lys Tyr
            355                 360                 365

TGC TGT GAC ATC AAT GGG TTT TCC TCT CTA AAT CTA ACA AAA CTT GAT        1152
Cys Cys Asp Ile Asn Gly Phe Ser Ser Leu Asn Leu Thr Lys Leu Asp
370                 375                 380

GTT CTG TCC GGG TTA CCA GAA ATT AAG CTG GGT GTT TCT TAT AAT CAA        1200
Val Leu Ser Gly Leu Pro Glu Ile Lys Leu Gly Val Ser Tyr Asn Gln
385                 390                 395                 400
```

```
ATG GAT GGA GAG AAA CTA CAA TCC TTC CCA GGG GAT CTT GAC ACC CTG         1248
Met Asp Gly Glu Lys Leu Gln Ser Phe Pro Gly Asp Leu Asp Thr Leu
            405                 410                 415

GAG CAA GTA CAG GTC AAC TAT GAG GTG CTT CCT GGG TGG GAC AGT GAC         1296
Glu Gln Val Gln Val Asn Tyr Glu Val Leu Pro Gly Trp Asp Ser Asp
            420                 425                 430

ATA TCT TCT GTC CGA AGT TAC AGT GAA CTC CCC CAA GCT GCC CGC CGT         1344
Ile Ser Ser Val Arg Ser Tyr Ser Glu Leu Pro Gln Ala Ala Arg Arg
            435                 440                 445

TAC GTG GAG AGG ATA GAA GAG CTC GCC GGT GTT CCA GTC CAC TAC ATT         1392
Tyr Val Glu Arg Ile Glu Glu Leu Ala Gly Val Pro Val His Tyr Ile
            450                 455                 460

GGT GTC GGG CCT GGG AGG GAT GCT CTG ATA TAC AAG TAAAGGGCAA              1438
Gly Val Gly Pro Gly Arg Asp Ala Leu Ile Tyr Lys
465                 470                 475

ACTCGATTTG GTACTATTGT ATCGGACGAA ATAATTCAGT CTTAACTAGG CCGTTGTGAG       1498

CATTGCTGTG TCAGCACACC CTTGATTGCC AATCGTAGCG GGTAATACGA TCGACAAGCT       1558

ACTGGCGGGC GGGGTGATGT AATACCTGCA ATAATGATTT CCGGGAAATG TCCCGATATA       1618

TCACCATAAG GATGCAGTGT TAGAGTTTGG TGGTAACATT TTGTCTTTCG ACTCCACCAA       1678

TGGTTTGGTG GTATTATCAC AATTCACCGT CAAAAAAAAA AAAAAAAAAA AAAAAAAAA        1738

AAA                                                                     1741
```

( 2 ) INFORMATION FOR SEQ ID NO:6:

( i ) SEQUENCE CHARACTERISTICS:
        ( A ) LENGTH: 476 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Ala Ala Ala Ala Ala Gly Arg Gly Arg Ser Phe Ser Pro Ala Ala Pro
  1               5                  10                  15

Ala Pro Ser Ser Val Arg Leu Pro Gly Arg Gln Ala Pro Ala Pro Ala
                 20                  25                  30

Ala Ala Ser Ala Leu Ala Val Glu Ala Asp Pro Ala Ala Asp Arg Val
             35                  40                  45

Ser Ser Leu Ser Gln Val Ser Gly Val Leu Gly Ser Gln Trp Gly Asp
 50                  55                  60

Glu Gly Lys Gly Lys Leu Val Asp Val Leu Ala Pro Arg Phe Asp Ile
 65                  70                  75                  80

Val Ala Arg Cys Gln Gly Ala Asn Ala Gly His Thr Ile Tyr Asn
                     85                  90                  95

Ser Glu Gly Lys Lys Phe Ala Leu His Leu Val Pro Ser Gly Ile Leu
                100                 105                 110

His Glu Gly Thr Leu Cys Val Val Gly Asn Gly Ala Val Ile His Val
                115                 120                 125

Pro Gly Phe Phe Gly Glu Ile Asp Gly Leu Gln Ser Asn Gly Val Ser
            130                 135                 140

Cys Asp Gly Arg Ile Leu Val Ser Asp Arg Ala His Leu Leu Phe Asp
145                 150                 155                 160

Leu His Gln Thr Val Asp Gly Leu Arg Glu Ala Glu Leu Ala Asn Ser
                165                 170                 175

Phe Ile Gly Thr Thr Lys Arg Gly Ile Gly Pro Cys Tyr Ser Ser Lys
                180                 185                 190
```

```
Val  Thr  Arg  Asn  Gly  Leu  Arg  Val  Cys  Asp  Leu  Arg  His  Met  Asp  Thr
          195                      200                      205

Phe  Gly  Asp  Lys  Leu  Asp  Val  Leu  Phe  Glu  Asp  Ala  Ala  Ala  Arg  Phe
     210                      215                     220

Glu  Gly  Phe  Lys  Tyr  Ser  Lys  Gly  Met  Leu  Lys  Glu  Glu  Val  Glu  Arg
225                      230                     235                           240

Tyr  Lys  Arg  Phe  Ala  Glu  Arg  Leu  Glu  Pro  Phe  Ile  Ala  Asp  Thr  Val
               245                      250                           255

His  Val  Leu  Asn  Glu  Ser  Ile  Arg  Gln  Lys  Lys  Lys  Ile  Leu  Val  Glu
               260                      265                      270

Gly  Gly  Gln  Ala  Thr  Met  Leu  Asp  Ile  Asp  Phe  Gly  Thr  Tyr  Pro  Phe
          275                      280                     285

Val  Thr  Ser  Ser  Ser  Pro  Ser  Ala  Gly  Gly  Ile  Cys  Thr  Gly  Leu  Gly
     290                      295                     300

Ile  Ala  Pro  Arg  Val  Ile  Gly  Asp  Leu  Ile  Gly  Val  Val  Lys  Ala  Tyr
305                      310                     315                           320

Thr  Thr  Arg  Val  Gly  Ser  Gly  Pro  Phe  Pro  Thr  Glu  Leu  Leu  Gly  Glu
               325                      330                           335

Glu  Gly  Asp  Val  Leu  Arg  Lys  Ala  Gly  Met  Glu  Phe  Gly  Thr  Thr  Thr
               340                      345                     350

Gly  Arg  Pro  Arg  Arg  Cys  Gly  Trp  Leu  Asp  Ile  Val  Ala  Leu  Lys  Tyr
          355                      360                     365

Cys  Cys  Asp  Ile  Asn  Gly  Phe  Ser  Ser  Leu  Asn  Leu  Thr  Lys  Leu  Asp
     370                      375                     380

Val  Leu  Ser  Gly  Leu  Pro  Glu  Ile  Lys  Leu  Gly  Val  Ser  Tyr  Asn  Gln
385                      390                     395                           400

Met  Asp  Gly  Glu  Lys  Leu  Gln  Ser  Phe  Pro  Gly  Asp  Leu  Asp  Thr  Leu
                405                                410                     415

Glu  Gln  Val  Gln  Val  Asn  Tyr  Glu  Val  Leu  Pro  Gly  Trp  Asp  Ser  Asp
               420                      425                     430

Ile  Ser  Ser  Val  Arg  Ser  Tyr  Ser  Glu  Leu  Pro  Gln  Ala  Ala  Arg  Arg
          435                      440                     445

Tyr  Val  Glu  Arg  Ile  Glu  Glu  Leu  Ala  Gly  Val  Pro  Val  His  Tyr  Ile
     450                      455                     460

Gly  Val  Gly  Pro  Gly  Arg  Asp  Ala  Leu  Ile  Tyr  Lys
465                      470                     475
```